(12) United States Patent
Smits et al.

(10) Patent No.: US 7,388,121 B2
(45) Date of Patent: Jun. 17, 2008

(54) PROCESS TO SEPARATE BUTADIENE DIMERS

(75) Inventors: Hubertus A Smits, Maastricht (NL); Gerardus Wa Hangx, Weert (NL); Johan T Tinge, Sittard (NL); Michael S Doelman, Maastricht (NL)

(73) Assignee: DSM IP Assets B.V., Heerlen (NL)

( * ) Notice: Subject to any disclaimer, the term of this patent is extended or adjusted under 35 U.S.C. 154(b) by 545 days.

(21) Appl. No.: 10/498,885

(22) PCT Filed: Dec. 19, 2002

(86) PCT No.: PCT/NL02/00852

§ 371 (c)(1),
(2), (4) Date: Jan. 6, 2005

(87) PCT Pub. No.: WO03/055839

PCT Pub. Date: Jul. 10, 2003

(65) Prior Publication Data

US 2005/0109605 A1    May 26, 2005

(30) Foreign Application Priority Data

Dec. 21, 2001 (EP) .................................. 01205094

(51) Int. Cl.
*C07C 7/04* (2006.01)

(52) U.S. Cl. ........................ 585/864; 208/240; 208/291
(58) Field of Classification Search ................ 585/833, 585/864; 208/290, 291, 313
See application file for complete search history.

(56) References Cited

U.S. PATENT DOCUMENTS

| 4,259,520 A | | 3/1981 | Summer |
| 5,495,041 A | * | 2/1996 | Sielcken et al. ............ 560/207 |
| 5,693,851 A | * | 12/1997 | Sielcken et al. ............ 560/207 |
| 6,010,975 A | | 1/2000 | Liu |

FOREIGN PATENT DOCUMENTS

WO        95/06027        3/1995

* cited by examiner

*Primary Examiner*—Tam M. Nguyen
(74) *Attorney, Agent, or Firm*—Nixon & Vanderhye P.C.

(57) ABSTRACT

The invention relates to a process to separate butadiene dimers from a mixture comprising butadiene dimers and alkyl-3-pentenoate and/or isomers thereof wherein the butadiene dimers are separated from said mixture by distillation in the presence of an alcohol and in that the distillation is effected at a bottom temperature of between 80 and 200° C. Examples of frequent occurring butadiene dimers are 4-vinylcyclohexene and 1,3,7-octatriene. Examples of the alcohol are monohydroxy aliphatic alcohols.

22 Claims, 3 Drawing Sheets

PROCESS TO SEPARATE BUTADIENE DIMERS

CROSS REFERENCE TO RELATED APPLICATION

Figure 1:
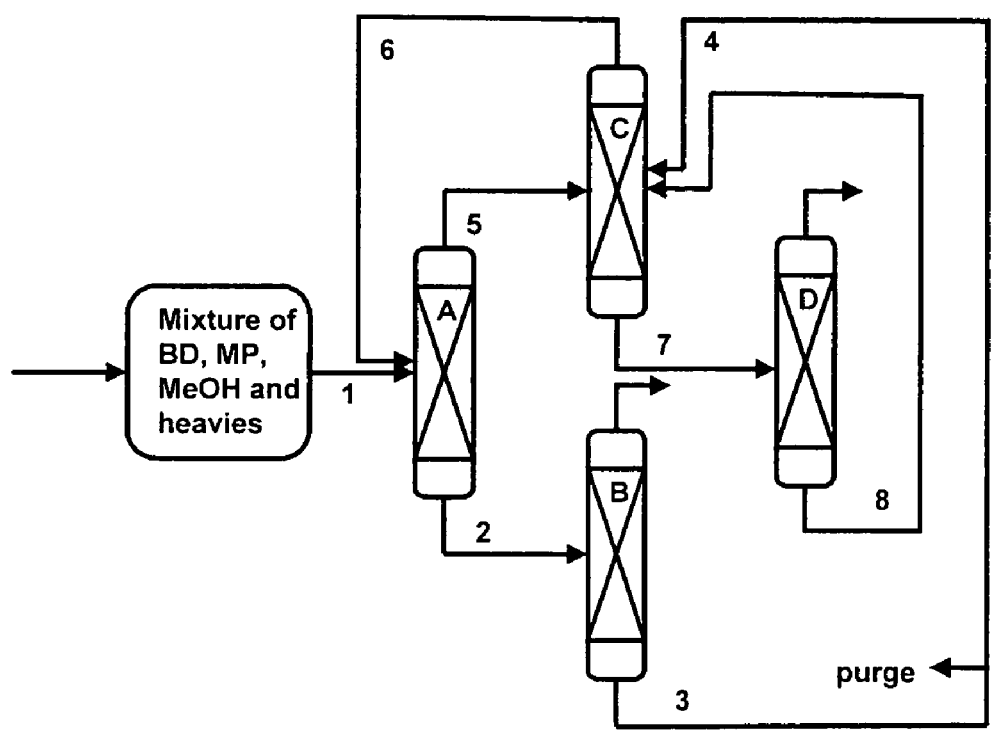

This application is the National Phase of International Application PCT/NL02/00852 filed Dec. 19, 2002 which designated the U.S., and was published in the English language.

The invention relates to a process to separate butadiene dimers from a mixture comprising butadiene dimers and alkyl-3-pentenoate and/or isomers thereof.

Such a mixture is for example obtained by carbonylation of butadiene in the presence of an alcohol, described in WO-A-9506027 and EP-B-728732. Butadiene dimers may for example be present as impurities in the butadiene feed and/or may be formed during the catalysed carbonylation reaction of butadiene. With butadiene dimers is meant any condensation product of two butadiene molecules. Examples of butadiene dimers are 1-vinylcyclohexene, 1,5-cyclooctadiene, 4-vinylcyclohexene and 1,3,7-octatriene. Frequent occurring butadiene dimers are 4-vinylcyclohexene and 1,3,7-octatriene. The prior art does not provide a method for the separation of butadiene dimers from a mixture comprising butadiene dimers and alkyl-3-pentenoate and/or isomers thereof. However, the presence of a substantial amount of butadiene dimers in such mixtures is unacceptable as butadiene dimers can act as catalyst poison or inhibitor in subsequent catalysed reactions of alkyl-3-pentenoate and/or isomers thereof, wherein metal catalysts are being used. An example of such a subsequent catalysed reaction is the hydroformylation of alkyl-3-pentenoate in the presence of a catalyst comprising e.g. rhodium and an organic phosphorous containing ligand to produce alkyl-5-formyl-valerate, an intermediate in the preparation of $\epsilon$-caprolactam. Butadiene dimers can form a complex with the metal of the catalyst blocking the coordination sites of the catalyst. Thus the resulting metal butadiene complex prevents that the alkyl-3-pentenoate enters the desired reaction pathway of hydroformylation, as such a pathway would require the energetically favoured coordinated butadiene dimer to be first displaced prior to reacting with the alkyl-3-pentenoate, carbon monoxide and hydrogen, the desired reaction pathway. Thus, to be reacted in a subsequent reaction step, it is essential that the alkyl-3-pentenoate and/or isomers thereof is of high purity. Separation of butadiene dimers from a mixture comprising butadiene dimers and alkyl-3-pentenoate and/or isomers thereof by distillation is unsuitable on industrial scale since the boiling points of butadiene dimers and alkyl-3-pentenoate and/or isomers thereof are close to each other. For example the boiling point at atmospheric pressure of 1,3,7-octatriene is 125° C., of methyl-4-pentenoate is 126° C., of 4-vinylcyclohexene is 128° C., of 1,5-cyclooctadiene is 132° C., of methyl-3-pentenoate is 136° C. and of 1-vinylcyclohexene is 145° C.

The object of the invention is to provide a method for the separation of butadiene dimers from a mixture comprising butadiene dimers and alkyl-3-pentenoate and/or isomers thereof.

This object is achieved in that the butadiene dimers are separated from said mixture by distillation in the presence of an alcohol and in that the distillation is effected at a bottom temperature of between 80 and 200° C.

Surprisingly, it has been found that distillation of a mixture comprising butadiene dimers and alkyl-3-pentenoate and/or isomers thereof in the presence of an alcohol and using a distillation bottom temperature of between 80 and 200° C. results in a separation of butadiene dimers from a mixture comprising butadiene dimers and alkyl-3-pentenoate and/or isomers thereof.

It has been found that distillation of the mixture comprising butadiene dimers and alkyl-3-pentenoate and/or isomers thereof in the presence of an alcohol using a distillation bottom temperature between 80 and 200° C. during the distillation surprisingly results in the formation of a butadiene dimers/alcohol mixture having a boiling point substantial lower than the boiling point of the alkyl-3-pentenoate. With a substantial lower boiling point is meant a boiling point at atmospheric pressure of at least 35° C. below the boiling point of the alkyl-3-pentenoate at atmospheric pressure.

Distillation of the mixture comprising butadiene dimers and alkyl-3-pentenoate and/or isomers thereof is performed with a bottom temperature between 80 and 200° C. Preferably, the bottom temperature is between 90 and 170° C. More preferably, the bottom temperature is between 100 and 150° C.

Alcohols which are employable in the process of the present invention will be well known compounds which are in general readily commercial available. Any alcohol that at atmospheric pressure has a boiling point that is at least 20° C. lower than the boiling point of the alkyl-3-pentenoate at atmospheric pressure can be used in the process of the invention. Preferably, the boiling point of the alcohol at atmospheric pressure is at least 30° C. lower than the boiling point of the alkyl-3-pentenoate at atmospheric pressure. A larger difference between the boiling point of the alkyl-3-pentenoate and that of the alcohol results in a more efficient separation of the butadiene dimers.

Preferably, the alcohol is a monohydroxy aliphatic alcohol. More preferably, the alcohol is a monohydroxy aliphatic C1-C4 alkyl alcohol. Examples are methanol, ethanol, 1-propanol, 2-propanol, 2-methyl-1-propanol, 1-butanol, 2-butanol, i-butanol. Most preferably the alcohol is methanol.

Preferably, the aliphatic group of the alcohol corresponds with the alkyl group of the alkyl pentenoate compound. With an alkyl pentenoate compound is meant an alkyl-3-pentenoate or an isomer thereof. The use of an alcohol corresponding with the alkyl group of the alkyl-pentenoate compound is especially advantageous since then transesterification of the alkyl pentenoate compound with the alcohol does not result in a different alkyl pentenoate compound; different with respect to the alkyl group. For example in the case that butadiene dimers have to be separated from a mixture comprising butadiene dimers and methyl-3-pentenoate and/or isomers thereof the use of methanol is preferred.

The amount of the alcohol present in the mixture according to the invention is preferably an effective amount to form a butadiene dimers/alcohol mixture having a boiling point substantial lower than the boiling point of alkyl-3-pentenoate. Preferably the distillation is performed in the presence of an excess molar amount of alcohol relative to the molar amount of butadiene dimers. Preferably, the molar amount of alcohol to the molar amount of butadiene dimers is at least 10 to 1.

The process of the present invention is performed in a distillation column. The column may be any distillation column.

The distillation of the process of the present invention preferably is as a vacuum distillation. Preferably the vacuum distillation is performed at a pressure between 0.001 MPa and 0.1 MPa, more preferably at a pressure between 0.01 MPa and 0.1 MPa. As used herein the pressure refers to the pressure at the top of the distillation column. A lower pressure is preferred since at a lower pressure a lower amount of alcohol can be used without deteriorating the separation of butadiene dimers from a mixture comprising butadiene dimers and alkyl-3-pentenoate and/or isomers thereof. From an economical point of view a higher pressure is preferred, since at a lower pressure a more expensive distillation equipment is required.

The mixture comprising butadiene dimers and alkyl-3-pentenoate and/or isomers thereof may be fed to the distillation column anywhere. The higher the feeding point of the mixture to be treated the better the separation between butadiene dimers and alkyl-3-pentenoate and/or isomers thereof will be.

The alcohol may be present in the mixture that is fed to the distillation column and/or may be fed to the distillation column in a separate stream. Preferably such a separate alcohol stream is fed below or at the same height of the feeding point of the mixture to be treated with the process of the present invention, in order to obtain an optimal interaction between the mixture and the alcohol.

Mixtures comprising butadiene dimers and alkyl pentenoate may for example be obtained by carbonylation of butadiene in the presence of an alcohol. Exemplifying carbonylation processes are e.g. described in WO-A-9506027 and EP-B-728732.

Suitable mixtures that can be treated with the process of the present invention are carbonylation reactor effluents or mixtures obtained after having separated the catalyst system. Depending on the source of the mixture, the mixture of the present invention may comprise compounds such as a catalyst system and/or heavies. Heavies are compounds having a boiling point higher than the boiling point of M3P.

The amount of butadiene dimers present in the mixture according to the invention generally lies in the range of 0.0001%-10% by weight. Usually the amount of butadiene dimers is between 0.001%-5% by weight, and in particular between 0.01%-2% by weight.

The alkyl-3-pentenoate can be represented by the following structural formula:

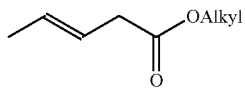

in which the alkyl group is a $C_1$-$C_4$ alkyl group. Examples are methyl, ethyl, propyl, iso-propyl, n-butyl, iso-butyl or t-butyl. The isomers of alkyl-3-pentenoate are alkyl-2-pentenoate and alkyl-4-pentenoate. The amount of alkyl-3-pentenoates and/or isomers thereof present in the mixture according to the invention is not critical, general, it lies in the range of 10-90% by weight.

The butadiene dimers/alcohol mixture obtained by the process of the present invention may be discarded or may be partly discarded and partly recycled for example into a carbonylation reactor in which butadiene is carbonylated in the presence of an alcohol to an alkyl pentenoate. Preferably, the butadiene dimers/alcohol mixture obtained with the process of the present invention is further subjected to a separation stage. Surprisingly it has been found that such separation can advantageously be performed by distilling the butadiene dimers/alcohol mixture in the presence of dialkyl adipate resulting in a top fraction comprising most of the alcohol and a bottom section comprising most of the butadiene dimers and the dialkyl adipate. The top fraction of this distillation may advantageously be recycled to a carbonylation reactor in which butadiene is carbonylated in the presence of an alcohol or it may be used to be fed to the distillation column in which butadiene dimers are separated from alkyl-3-pentenoate and/or isomers thereof. The bottom fraction of the distillation column in which butadiene dimers are separated from the alcohol is preferably further treated in a distillation column resulting in a top fraction comprising most of the butadiene dimers and a bottom fraction comprising most of the dialkyl adipate. This bottom fraction is advantageously recycled to the distillation column in which butadiene dimers are separated from the alcohol.

Dialkyl adipate is a compound that for example can be formed through carbonylation of alkyl-4-pentenoate in the presence of an alcohol. For example, dimethyl adipate is formed as a by-product during carbonylation of butadiene in the presence of methanol aimed at the formation of methyl-3-pentenoate.

The process of the present invention will be described in more detail for the following preferred embodiment. It shall be evident that the below stated conditions will also be applicable for the above described mixtures in a manner clear to one skilled in the art.

Referring to FIG. 1, a mixture comprising butadiene dimers (BD), methyl-3-pentenoate and/or isomers thereof (MP), methanol (MeOH) and high boiling compounds (heavies) including dimethyl adipate (DMA) is fed to distillation column A through line 1. The bottom fraction of distillation column A is fed to distillation column B through line 2. In distillation column B, MP is separated from the heavies. The heavies are leaving distillation column B through line 3 and are partly purged and partly fed to distillation column C through line 4. The top fraction of distillation column A, comprising a BD/MeOH mixture, is fed to distillation column C through line 5. In distillation column C MeOH is separated from BD in the presence of DMA. The thus separated MeOH is preferably recycled to distillation column A, through line 6. The bottom fraction of distillation column C, comprising BD and DMA, is fed to distillation column D through line 7. In distillation column D DMA is separated from BD. The thus obtained DMA is preferably recycled to distillation column C through line 8.

The invention will be elucidated by the following non-restrictive examples I-IV.

EXAMPLES

Figure 2:
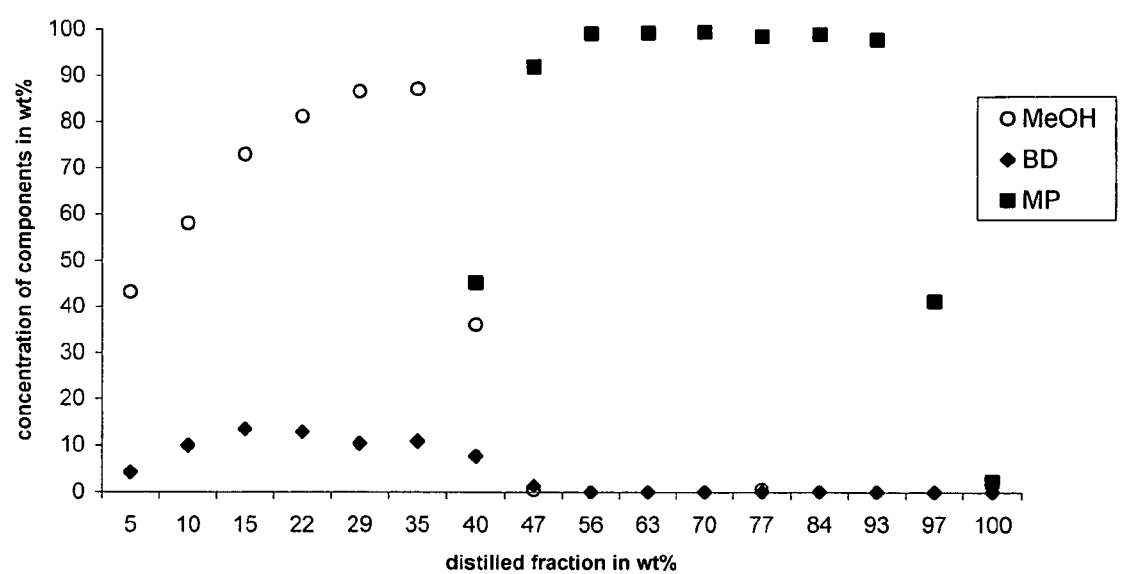

Example I 202 g of a mixture comprising 3.3% by weight of 4-vinylcyclohexene (VCH), 0.4% by weight of 1,3,7-octatriene (OCT), 41.6% by weight of methyl-3-pentenoate (M3P) and isomers thereof (M2P and M4P) and 27% by weight of methanol was distilled in a batch-wise operated distillation column having 35 equilibrium stages at a reflux ratio of 10 and at a pressure of 0.01 MPa. The starting mixture also comprises 4.8% by weight of butadiene, 8.6% by weight of methoxy butenes, 7.2% by weight of dimethyl adipate and 7.1% by weight of other compounds. Distillation fractions of 5-7 wt % relative to the total mixture were isolated and analysed by means of Gas Chromatography. The results are presented in FIG. 2 for methanol (MeOH), butadiene dimers (BD), i.e. the sum of VCH and OCT, M3P and/or isomers thereof (MP), i.e. the sum of M3P, M2P and M4P. These results show that first distillation fractions containing methanol, 4-vinylcyclohexene and 1,3,7-octatriene are distilled off and subsequently distillation fractions containing methyl-3-pentenoate and isomers thereof.

Example II

Figure 3:
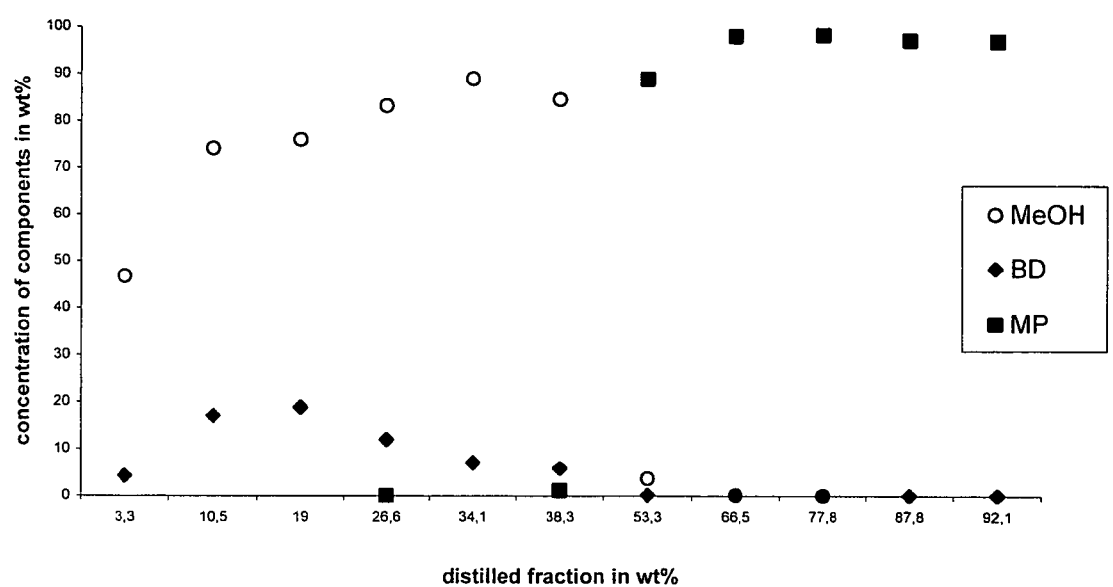

Example I was repeated except that 102 g of a mixture comprising 4.4% by weight of 4-vinylcyclohexene (VCH), 0.5% by weight of 1,3,7-octatriene (OCT), 54.7% by weight of methyl-3-pentenoate (M3P) and isomers thereof (M2P and M4P) and 33% by weight of methanol was distilled at a pressure of 0.05 MPa. The starting mixture also comprises 6.3% by weight of methoxybutenes and 1.1% by weight of other compounds. Again first distillation fractions containing methanol, 4-vinylcyclohexene and 1,3,7-octatriene are distilled off and subsequently distillation fractions containing methyl-3-pentenoate and isomers thereof. The results are given in FIG. 3 for methanol (MeOH), butadiene dimers (BD), i.e. the sum of VCH and OCT, M3P and/or isomers thereof (MP), i.e. the sum of M3P, M2P and M4P.

Example III

A mixture comprising 0.4% by weight of 4-vinylcyclohexene (VCH), 0.1% by weight of 1,3,7-octatriene (OCT), 37.7% by weight of methyl-3-pentenoate (M3P) and isomers thereof (M2P and M4P) and 37% by weight of methanol was fed to the top of a continuous operated distillation column in an amount of 2.5 kg/h. The distillation column was a column packed with 5 meter Sulzer BX structured packing®, having 30-35 equilibrium stages and a diameter of 5 cm. The distillation was performed without an external flux at a pressure of 0.045 MPa and a temperature of 120° C. at the bottom of the column and 45° C. at the top of the column.

The results are given in Table I and show that the butadiene dimers are distilled off together with the methanol (Table I, example III, distillate data) and that the bottom stream containing methyl-3-pentenoate and isomers thereof contains less than 0.0002 wt % of butadiene dimers (Table I, example III, bottom stream data).

Example IV

Example III was repeated except that the distillation column was a column packed with 2.5 meter Sulzer BX structured packing®, having 15-18 equilibrium stages. The results are also given in Table I and show again that the butadiene dimers are distilled off together with the methanol (Table I, example IV, distillate data) and that the bottom stream containing methyl-3-pentenoate and isomers thereof contains less than 0.0002 wt % of butadiene dimers (Table I, example IV, bottom stream data).

TABLE I

Concentration of components in different mixtures in wt %

| | Example | | | | | |
|---|---|---|---|---|---|---|
| | III | | | IV | | |
| | Mixture | | | | | |
| Component | Feed | Bottom stream | Distillate | Feed | Bottom stream | Distillate |
| MeOH | 37.0 | 0 | 75.0 | 31 | 0 | 69.8 |
| MB* | 9.3 | 0 | 16.3 | 8.6 | 0 | 15.7 |
| VCH | 0.4 | <0.0002 | 1.0 | 1.7 | <0.0002 | 3.5 |
| OCT | 0.1 | <0.0002 | 0.1 | 0.2 | <0.0002 | 0.4 |
| M3P | 36.0 | 68.1 | 5.5 | 36.7 | 67.1 | 3.1 |
| M2P | 2.1 | 4.1 | 0.3 | 2.6 | 5.1 | 0.2 |
| M4P | 0.3 | 0.5 | 0.1 | 0.4 | 0.2 | 0.9 |
| DMA** | 8.0 | 16.6 | 0 | 7.5 | 15.1 | 0 |
| DMES# | 0.3 | 0.7 | 0 | 0.2 | 0.5 | 0 |
| Heavies## | 6.5 | 10.0 | 1.7 | 11.1 | 12.0 | 6.4 |

*MB = methoxy butenes
**DMA = dimethyl adipate
DMES = dimethyl succinate
Heavies = high boiling compounds, i.e. compounds having a boiling point higher than the boiling point of M3P

The invention claimed is:

1. Process to separate butadiene dimers from a mixture comprising butadiene dimers and alkyl-3-pentenoate and/or isomers thereof, the process comprising separating the butadiene dimers from the mixture by distilling the mixture in the presence of an alcohol and at a distillation bottom temperature of between 80 and 200° C.

2. Process according to claim 1 wherein the boiling point of the alcohol is at least 20° C. lower than the boiling point of the alkyl-3-pentenoate at atmospheric pressure.

3. Process according to claim 2 wherein the boiling point of the alcohol is at least 30° C. lower than the boiling point of the alkyl-3-pentenoate at atmospheric pressure.

4. Process according to claim 1 wherein the alcohol is a monohydroxy aliphatic alcohol.

5. Process according to claim 4 wherein the alcohol is methanol.

6. Process according to claim 1, wherein the aliphatic group of the alcohol corresponds with the alkyl group of the alkyl pentenoate compound.

7. Process according to claim 1 comprising distilling the mixture in the presence of an excess amount of alcohol relative to the molar amount of butadiene dimers.

8. Process according to claim 1, comprising distilling the mixture by vacuum distillation.

9. Process according to claim 8 comprising performing the vacuum distillation at a pressure between 0.001 and 0.1 MPa.

10. Process according to claim 1, wherein the butadiene dimer is 4-vinylcyclohexene and/or 1,3,7-octatriene, the alkyl-3-pentenoate is methyl-3-pentenoate and the alcohol is methanol.

11. Process according to claim 1, comprising separating butadiene dimers from the mixture of butadiene dimers and alcohol by distilling the mixture in the presence of dialkyl adipate.

12. Process according to claim 11 wherein the dialkyl adipate is dimethyl adipate.

13. Process to separate butadiene dimers from a mixture comprising butadiene dimers and alkyl-3-pentenoate and/or isomers thereof, the process comprising separating the butadiene dimers from the mixture by distilling the mixture in the presence of an excess amount of alcohol relative to the molar amount of butadiene dimers, the alcohol having a boiling point which is at least 20° C. lower than the boiling point of the alkyl-3-pentenoate at atmospheric pressure, and at a distillation bottom temperature of between 80 and 200° C.

14. Process according to claim 13 wherein the boiling point of the alcohol is at least 30° C. lower than the boiling point of the alkyl-3-pentenoate at atmospheric pressure.

15. Process according to claim 13 wherein the alcohol is a monohydroxy aliphatic alcohol.

16. Process according to claim 15 wherein the alcohol is methanol.

17. Process according to claim 13, wherein the aliphatic group of the alcohol corresponds with the alkyl group of the alkyl pentenoate compound.

18. Process according to claim 13, comprising distilling the mixture by vacuum distillation.

19. Process according to claim 18 comprising performing the vacuum distillation at a pressure between 0.001 and 0.1 MPa.

20. Process according to claim 13, wherein the butadiene dimer is 4-vinylcyclohexene and/or 1,3,7-octatriene, the alkyl-3-pentenoate is methyl-3-pentenoate and the alcohol is methanol.

21. Process according to claim 13, comprising separating butadiene dimers from the mixture of butadiene dimers and alcohol by distilling the mixture of butadiene dimers and alcohol in the presence of dialkyl adipate.

22. Process according to claim 21 wherein the dialkyl adipate is dimethyl adipate.

* * * * *